US008676556B2

(12) United States Patent
Deffenbaugh et al.

(10) Patent No.: US 8,676,556 B2
(45) Date of Patent: Mar. 18, 2014

(54) METHOD FOR DETERMINING THE PROPERTIES OF HYDROCARBON RESERVOIRS FROM GEOPHYSICAL DATA

(75) Inventors: Max Deffenbaugh, Califon, NJ (US); John H. Dunsmuir, Flemington, NJ (US); Limin Song, West Windsor, NJ (US); Ganglin Chen, Houston, TX (US); Shiyu Xu, Kingwood, TX (US); Michael A. Payne, Spring, TX (US); Enru Liu, Sugar Land, TX (US)

(73) Assignee: ExxonMobil Upstream Research Company, Houston, TX (US)

( * ) Notice: Subject to any disclaimer, the term of this patent is extended or adjusted under 35 U.S.C. 154(b) by 470 days.

(21) Appl. No.: 12/678,580

(22) PCT Filed: Sep. 11, 2008

(86) PCT No.: PCT/US2008/075920
§ 371 (c)(1),
(2), (4) Date: Mar. 17, 2010

(87) PCT Pub. No.: WO2009/070365
PCT Pub. Date: Jun. 4, 2009

(65) Prior Publication Data
US 2010/0198638 A1 Aug. 5, 2010

Related U.S. Application Data

(60) Provisional application No. 61/004,336, filed on Nov. 27, 2007.

(51) Int. Cl.
*G06G 7/48* (2006.01)
(52) U.S. Cl.
USPC .......................................................... 703/10

(58) Field of Classification Search
USPC .......................................................... 703/10
See application file for complete search history.

(56) References Cited

U.S. PATENT DOCUMENTS

| 5,077,697 | A | 12/1991 | Chang |
| 5,444,619 | A | 8/1995 | Hoskins et al. |
| 5,659,135 | A | 8/1997 | Cacas |
| 5,675,147 | A | 10/1997 | Ekstrom et al. |
| 5,828,981 | A | 10/1998 | Callender et al. |
| 5,838,634 | A | 11/1998 | Jones et al. |
| 5,869,755 | A | 2/1999 | Ramamoorthy et al. |

(Continued)

OTHER PUBLICATIONS

Gleeson Abstract of SPE document ID 20493-PA "NMR Imaging of Pore Structures in Limestones".*

(Continued)

*Primary Examiner* — Saif Alhija
(74) *Attorney, Agent, or Firm* — ExxonMobil Upstream Research Company Law Dept.

(57) ABSTRACT

A hydrocarbon exploration method is disclosed for developing a model of at least one effective material property of a subsurface reservoir as a function of the composition and structure of the reservoir rock. In one embodiment, the method comprises: obtaining a 3D image (102) of a rock sample characteristic of a reservoir of interest (101); segmenting the 3D image into compositional classes (103) based on similarities in mineralogy, structure and spatial distribution; selecting a model (105) that relates an effective material property of interest to the volume fractions of each compositional class; and determining the parameters of the model (106). The model may be used to assess the commercial potential of the subsurface reservoir (107).

23 Claims, 6 Drawing Sheets

(56) References Cited

U.S. PATENT DOCUMENTS

| | | | |
|---|---|---|---|
| 6,061,300 A | 5/2000 | Yamamoto | |
| 6,088,656 A | 7/2000 | Ramakrishnan et al. | |
| 6,091,669 A | 7/2000 | Chen | |
| 6,289,284 B1 | 9/2001 | Yamamoto | |
| 6,374,185 B1 | 4/2002 | Taner et al. | |
| 6,401,042 B1 | 6/2002 | Van Riel et al. | |
| 6,470,274 B1 | 10/2002 | Mollison et al. | |
| 6,473,696 B1 | 10/2002 | Onyia et al. | |
| 6,493,632 B1 | 12/2002 | Mollison et al. | |
| 6,516,080 B1 | 2/2003 | Nur | |
| 6,529,833 B2 | 3/2003 | Fanini et al. | |
| 6,674,432 B2 | 1/2004 | Kennon et al. | |
| 6,711,502 B2 | 3/2004 | Mollison et al. | |
| 6,715,551 B2 | 4/2004 | Curtis et al. | |
| 6,718,265 B2 | 4/2004 | Herron et al. | |
| 6,751,558 B2 | 6/2004 | Huffman et al. | |
| 6,795,773 B2 | 9/2004 | Soliman et al. | |
| 6,904,365 B2 | 6/2005 | Bratton et al. | |
| 6,941,255 B2 | 9/2005 | Kennon et al. | |
| 6,959,246 B2 | 10/2005 | Herron | |
| 6,977,866 B2 | 12/2005 | Huffman et al. | |
| 6,980,940 B1 | 12/2005 | Gurpinar et al. | |
| 6,987,385 B2 | 1/2006 | Akkurt et al. | |
| 7,006,951 B2 | 2/2006 | Pond, Jr. et al. | |
| 7,027,964 B2 | 4/2006 | Kennon | |
| 7,043,413 B2 | 5/2006 | Ward et al. | |
| 7,111,681 B2 | 9/2006 | Detournay et al. | |
| 7,149,671 B2 | 12/2006 | Lim et al. | |
| 7,257,490 B2 | 8/2007 | Georgi et al. | |
| 7,260,508 B2 | 8/2007 | Lim et al. | |
| 7,277,795 B2 | 10/2007 | Boitnott | |
| 7,286,939 B2 | 10/2007 | Bachrach et al. | |
| 7,356,413 B2 | 4/2008 | Georgi et al. | |
| 7,363,161 B2 | 4/2008 | Georgi et al. | |
| 7,369,973 B2 | 5/2008 | Kennon et al. | |
| 7,472,588 B2 | 1/2009 | Slavin et al. | |
| 7,516,016 B2 | 4/2009 | DeMartini et al. | |
| 7,746,725 B2 | 6/2010 | Akhtar | |
| 7,825,659 B2 | 11/2010 | Georgi et al. | |
| 7,859,943 B2 | 12/2010 | Herwanger | |
| 8,090,555 B2 | 1/2012 | Dai et al. | |
| 8,195,399 B2 | 6/2012 | Gladkikh et al. | |
| 2002/0067373 A1 | 6/2002 | Roe et al. | |
| 2005/0074834 A1 | 4/2005 | Chaplen et al. | |
| 2006/0144587 A1 | 7/2006 | Detournay et al. | |
| 2006/0153005 A1 | 7/2006 | Herwanger et al. | |
| 2006/0219402 A1 | 10/2006 | Lecampion | |
| 2007/0255500 A1* | 11/2007 | Pita et al. | 702/11 |
| 2009/0043554 A1 | 2/2009 | Horne et al. | |

OTHER PUBLICATIONS

Arns, C.H. et al., (2002), Computation of linear elastic properties from microtomographic images: Methodology and agreement between theory and experiment, Geophysics, 67, pp. 1396-1405.

Arns, C.H. et al., (2004), "Virtual permeametry on microtomographic images", J. Petroleum Science and Engineering, 45, pp. 41-46.

Bencsik, M. et al., (2001), "Method for measuring local hydraulic permeability using magnetic resonance imaging", Phys. Rev. E, 63, 065302.

Berryman, J.G., (1979), "Explicit schemes for estimating elastic properties of multiphase composites", Stanford Exploration Project Report No. 79, pp. 229-244.

Brinkman, H.C., (1947), "A calculation of the viscous force exerted by a flowing fluid on a dense swarm of particles", Appl. Sci. Res. A1, pp. 27-34.

Dvorkin, J. et al., (1996), "Elasticity of high-porosity sandstones: Theory for two North Sea data sets", Geophysics, 61, pp. 1363-1370.

Flannery, B.P. et al., (1987), "Three-dimensional x-ray microtomography" Science 237, pp. 1439-1444.

Fredrich, J.T., (1995), "Imaging the Pore Structure of Geomaterials", Science 268, 276-279.

Garboczi, E.J. et al., (2000), "New effective medium theory for the diffusivity and conductivity of a multi-scale concrete microstructural model", Concrete Science and Engineering, 2, pp. 88-96.

Greenberg, M.L. et al., (1992), "Shear wave velocity estimation in porous rocks: theoretical formulation, preliminary verification, and applications", Geophys. Prosp., 40, pp. 195-209.

Jakobsen, M., 1996, "The effective permeability of fractured reservoirs and composite porous media" Expanded Abstracts, $76^{th}$ Annual Meeting of the Society of Exploration Geophysicists, New Orleans, LA, pp. 1747-1751.

Keehm, Y. et al., (2001), "Computational rock physics at the pore scale: Transport properties and diagenesis in realistic pore geometries", The Leading Edge, 20, pp. 180-183

Knackstedt, M.A., et al. (2005), "Velocity-porosity relationships: Predictive velocity model for cemented sands composted of multiple mineral phases", Geophysical Propsecting, 53, pp. 349-372.

Koplik, J. et al., (1983), "Viscosity renormalization in the Brinkman equations", Phys. Fluids 26, pp. 2864-2870.

Kuster, G.T. et al., (1974), "Velocity and attenuation of seismic waves in two-phase media: Part I. Theoretical Formulations", Geophysics, 39, pp. 587-606

McLachlan, D.S. et al., (1990), "Electrical resistivity of composites", J. Am Ceram. Soc., 73, pp. 2187-2203.

Martys, N.S. (2001), "Improved approximation of the Brinkman equation using a lattice Boltzmann method" Phys. Fluids, 13, pp. 1807-1810.

Martys, N.S. et al., (1994), Computer simulation study of the effective viscosity in Brinkman's equations:, Phys Fluids 6, pp. 1434-1439.

Martys, N.S. et al., (1999), "Large Scale Simulations of Single and Multi-Component Flow in Porous Media", SPIE Conf. on Developments in X-Ray Tomography, Denver, CO, Jul. 1999, SPIE v. 3772, pp. 205-213.

Øren, P.E. et al., (2002), "Process based reconstruction of sandstones and prediction of transport properties" Transport in Porous Media 46, pp. 311-343.

Øren, P.E. et al., (2006), "Pore-scale computation of material and transport properties on North-Sea reservoir rocks", Computational Methods in Water Resources XVI, Copenhagen, Denmark, Jun. 19-22, 8 pgs.

Pozdniakov, S. (2004), "A self-consistent approach for calculating the effective hydraulic conductivity of a binary, heterogeneous medium", Water Resources Research, 40, W051005, 13 pgs.

Roberts, A.P. et al., (2000), "Elastic Properties of Model Porous Ceramics", J. American Ceramic Society, 83, pp. 3041-3048

Sen, P.N. et al., (1981), "A self-similar model for sedimentary rocks with application to the dielectric constant of fused glass beads", Geophysics, 46, pp. 781-795

Sheng, P., 1991, "Consistent modeling of the electrical and elastic properties of sedimentary rocks" Geophysics, 56, pp. 1236-1243.

Spanne, P.J., (1994) "Synchrotron computed microtomography of porous media: Topology and transports", Physical Review Letters, 73, pp. 2001-2004.

Torquato, S., (1999), "Effective conductivity, dielectric constant, and diffusion coefficient of digitized composite media via first-passage-time equations", J. Appl. Phys. 85, pp. 1560-1571.

Willis, J.R., (1977), "Bounds and self-consistent estimates for the overall properties of anisotropic composite", Journal of Mechanics and Physics of Solids, 25, pp. 85-202.

Worthington, P.F. (1985), "Evolution of shaley sand concepts in reservoir evaluation", The Log Analyst, 26, pp. 23-40.

Xu, S. et al. (2007), "Carbonate rock physics: analytical models and validations using computational approaches and lab/log measurements", XP002488785, Int'l. Petroleum Technology Conf., Dec. 5, 2007.

Xu, S. et al. (1995), "A new velocity model for clay-sand mixtures", Geophys. Prosp., 43, pp. 91-118.

Yeong, C.L.Y. et al., (1998). "Reconstructing Random Media" Physical Review E, 57, pp. 495-506.

Youseff, N. et al. (2007), "High Resolution CT and Pore-Network Models to Assess Petrophysical Properties of Homogeneous and Heterogenous Carbonates", SPE111427, 2007 SPE/EAG Reservoir Characterization and Simulation Conf., 12 pgs.

*European Search Report*, dated Aug. 4, 2008.

*International Search Report & Written Opinion*, dated Nov. 8, 2008.

\* cited by examiner

METHOD FOR DETERMINING THE PROPERTIES OF HYDROCARBON RESERVOIRS FROM GEOPHYSICAL DATA

This application is the National Stage entry under 35 U.S.C. 371 of PCT/US2008/075920 that published as WO 2009/070365 and was filed on 11 Sep. 2008, which claims the benefit of U.S. Provisional Application No. 61/004,336, filed on 27 Nov. 2007, each of which is incorporated by reference, in its entirety, for all purposes.

FIELD OF THE INVENTION

This invention relates generally to the field of geophysical prospecting. Specifically, the invention is a hydrocarbon exploration method for determining subsurface reservoir properties such as porosity, permeability, and pore fluid type from an effective material property sensed by geophysical surveys or log measurements.

BACKGROUND OF THE INVENTION

Hydrocarbon reservoirs are porous bodies of rock in the subsurface where the pore spaces within the rock are at least partly filled by hydrocarbons. Reservoir rocks are typically sedimentary rocks composed of several different classes of inclusions and voids. For example, in a siliciclastic rock, the compositional classes might be large quartz grains, small quartz grains, feldspar grains, calcite cement which binds the grains together, clay, and pore space between the grains. In a carbonate rock, the compositional classes might be shell fragments, skeletal remains, microporous regions, vugs, and intergranular pores. Within a single geologic formation or stratigraphic unit, rocks will typically contain the same compositional classes, though the volume fractions of each class may vary. Based on the geologic context of a new prospect, geologists can often predict the compositional classes that will be found in a prospective reservoir, though the volume fractions of each compositional class at a given location within the reservoir are typically unknown before drilling.

Since rocks within a single formation typically have the same compositional classes and similar pore-scale structure, rock samples from one location can often be used to predict relationships between properties at a different location in the same formation where a sample is not available. Rock samples from an analog formation, a different formation thought to have similar structure and composition, can also be used to predict relationships between properties in a formation of interest.

The composition and structure of a reservoir rock and the type of fluid in the pore space of the rock influence the reflection and transmission of seismic waves by the rock and the conductivity and dielectric constant of the rock. Relationships among seismic, electrical and reservoir properties are exploited in geophysical prospecting for hydrocarbons, where data from seismic or electromagnetic surveys are used to predict the spatially-varying properties of a reservoir. The predicted reservoir properties are the basis for decisions about how many wells to drill, the type of well to drill, and where the wells should be placed to optimally recover the resource from the reservoir.

Seismic properties of a reservoir rock are those properties that directly determine the reflection and transmission of seismic waves by the rock, and together define at least the compressional wave velocity, shear wave velocity, and density of the rock. It is often more convenient to express the seismic properties of a rock in terms of elastic properties, such as bulk modulus and shear modulus (also called the elastic moduli). Various functions of the velocities and density of the rock can be equivalently used to express seismic properties, including: bulk modulus, shear modulus, Poisson's ratio, Vp/Vs ratio, P-wave modulus, and Lamé parameters. Seismic properties may also include, for example, anisotropy and attenuation. Seismic wave velocities may vary with the frequency of the seismic wave, a phenomenon called dispersion. Among the seismic properties, density is a simple function of the volume fractions of compositional classes, being the volume-weighted average of the densities for each compositional class independent of the structure of the rock. By contrast, the relationship between elastic properties and volume fractions is complicated and will vary between different formations due to variations in structure.

Electrical properties of a reservoir rock are those that determine the electrical current that results from an applied electrical potential, and include at least the conductivity or resistivity of the rock. Electrical properties may also include, for example, the capacitance or dielectric constant of a reservoir rock, the frequency dependence of conductivity and dielectric constant, as well as anisotropy parameters associated with directional variation in conductivity and capacitance. Sometimes the effect of the rock matrix on conductivity is expressed by the formation factor, which is the ratio of the conductivity of the pore fluid to the conductivity of the fluid-saturated rock. The relationship between electrical properties and the volume fractions of the compositional classes in a rock is complicated and formation dependent since electrical properties also depend on structure.

Reservoir properties include the composition, pore-scale structure or texture, and pore fluid contents of the reservoir rock as it varies throughout the reservoir. Of direct importance to hydrocarbon production is the type of pore fluid and the porosity and permeability of the reservoir rock. The pore fluid type is oil, natural gas, ground water, or some combination of those. The porosity determines the volume of fluid in the reservoir. Often it is important to further distinguish between connected porosity which can be drained through a nearby well and unconnected porosity which cannot be drained at economically significant rates but may play a role over geologic time in determining the distribution of fluids in the reservoir. The permeability and its spatial distribution within the reservoir determine whether the fluid may be produced from the reservoir at an economically viable rate. Variability in the mineral composition and pore geometries of the reservoir rock can mask the effect of fluid type, porosity, and permeability on seismic and electrical properties. Thus accurate quantification of composition and pore geometries may also be necessary in order to determine pore fluid type, porosity, and permeability. Many reservoir properties may be directly expressed by the volume fractions of appropriately defined compositional classes in the reservoir rock. For example, porosity is simply the volume fraction of pore space, and mineral composition is given as the volume fraction of each mineral type, usually divided by the total mineral (non-pore) volume fraction. Pore fluid type may be directly expressed by volume fractions of water, oil, and gas within the pore space, and grain size distributions are expressed by the volume fractions of grains falling into each of several size ranges. By contrast, permeability depends on rock structure as well as the volume fractions of compositional classes. The relationship between permeability and the volume fractions of compositional classes that applies for one formation may not apply in a different formation with the same compositional classes due to differences in rock structure.

It is important to distinguish between the local properties at points within a rock sample and the effective medium (sometimes called bulk) properties of the sample taken as a whole. For example, a seismic wave velocity can be specified for the mineral or pore fluid at each point within the sample. However, seismic waves of interest have wavelengths much longer than the diameter of any grain or pore within the sample so they travel through the sample at an intermediate "effective" or "bulk" velocity which is a complicated average over the velocities of the compositional classes that make up the sample.

Relationships among seismic, electrical, and reservoir properties are used in predicting reservoir properties from geophysical survey data. In current practice, such relationships come from two sources: empirical studies and theoretical models. In empirical studies, rock samples are obtained from a geological analog, a formation thought to have similar properties to the reservoir. The effective properties of these samples are measured in the laboratory, and an empirical curve or surface is fit through the measured values that seems to characterize the relationship between the properties of interest. [e.g., Dvorkin and Nur, 1996] Sometimes down-hole measurements by well logging tools are used in lieu of or in combination with lab measurements to establish empirical relationships. [e.g., Greenberg & Castagna, 1992] The empirical relationship may be a simple curve fit or a more complicated one estimated by artificial neural networks. [Hoskins & Ronen, 1995] The relevance of empirical relationships depends on the extent to which the source of the rock samples resembles the prospective reservoir. The accuracy depends on whether the quantity and quality of the measurements are sufficient to discern the true relationship between the properties of interest. When a large number of properties must be included in the relationship, empirical methods are often unable to resolve their separate contributions.

In certain idealized cases, theoretical models give relationships between properties. For example, if a rock consists of a homogeneous background material with non-interacting spheroidal inclusions of other materials or pores, the relationship between the effective elastic moduli of the rock and the volume fractions of the inclusions can be calculated analytically. A theoretical model is available for this case because the idealized structure of this rock (spheroidal inclusions) is amenable to analytical calculations. This theoretical model is based on the elastic properties of the background material, the elastic properties of the inclusions, and the shape of the inclusions. For spheroidal inclusions, shape is fully characterized by specifying the aspect ratio. A spheroid is a three-dimensional shape formed by rotating an ellipse around one of its two axes, and the aspect ratio of the resulting spheroid is the ratio of the length of the axis of rotation to the length of the other axis of the ellipse. For example, for oblate spheroids, the axis of rotation is the minor axis of the ellipse, and the aspect ratio is less than one. A theoretical model for the elastic properties of a rock with spheroidal inclusions is given by Kuster & Toksöz [1974]. The Kuster-Toksöz (KT) model is only accurate for low concentrations of inclusions, but differential effective medium (DEM) theory teaches that the KT model can be applied with a process of iterative homogenization: adding an inclusion, calculating the effective properties, assuming a new homogeneous background with those properties, and repeating until all inclusions are added. This DEM theory approach provides accurate predictions out to higher volume fractions. An alternative to DEM theory is self-consistent (SC) theory which teaches that when small concentrations of each inclusion type are added (e.g., using KT theory) in correct proportion to a homogeneous background having the correct effective medium properties, then the addition does not change the effective medium properties. Under SC theory, values for background properties are tried until the addition of the inclusions leaves them unaltered. DEM and SC results are available for permeability and conductivity as well as elastic properties. [Torquato, 2002] The accuracy of theoretical models is limited by the extent to which the rocks conform to the assumptions of the model. The pores and inclusions within real rocks are not spheroidal and do not have well-defined aspect ratios, so theoretical models that assume otherwise must be applied with caution.

In practice, rock properties models often incorporate certain principles from theoretical models together with empirically determined parameters. For example, DEM or SC theory defines a certain family of curves relating effective properties of the rock to the volume fractions of each compositional class. The family of curves is parameterized by the aspect ratios of each compositional class. Although the aspect ratios for real inclusions are not well-defined and therefore cannot be calculated directly from rock images, effective aspect ratios may be selected for each compositional class to best fit the family of curves to lab measurements on actual rock samples. The physical constraints imposed by a theoretical model make it possible to determine property relationships from fewer rock samples than would be required in a purely empirical approach. Constraining the free parameters of a theoretical model typically requires at least as many rock samples as there are parameters, and generally many more due to measurement noise and model approximations. When a theoretical model has more than a few unknown parameters, these typically cannot be accurately determined from lab measurements of effective properties alone.

Another approach to determining relationships between seismic, electrical, and reservoir properties is to generate a set of virtual rock samples by simulating the processes by which siliciclastic rocks are formed: sedimentation, compaction, and diagenesis. [Øren & Bakke, 2002] Various seismic and reservoir properties may be computed for the virtual rock samples produced by the simulation and correlations between the properties explored. [Øren, Bakke, & Held, 2006] The limitation of this method is that the simulation may not accurately reproduce the structure and properties of real rocks. This is particularly a concern for carbonate rocks, where the processes of diagenesis are often more complicated than in siliciclastics.

Computational rock physics is the computation rather than laboratory measurement of seismic, electrical, or reservoir properties of a rock based on numerical simulation at the pore scale. In this technique, a 3D image is taken of a rock sample and a 3D digital representation of the rock is created. By assigning properties to the components of the digital rock and using fundamental physical principles, the effective properties of the rock sample can be computed numerically. When a 3D image is not available, a digital rock can be constructed statistically honoring spatial correlations extracted from a 2D image of the rock. [Nur, 2003] Of course, the digital rock can also be entirely computer generated without reference to an actual rock sample, and such a purely synthetic volume can still be useful for evaluating the idealized assumptions of theoretical models. [e.g., Knackstedt et al, 2005] Recent examples of computational rock physics include the computation of permeability from 3D images and statistical reconstructions from 2D images [Arms et al, 2004; Keehm et al, 2001], computation of effective bulk and shear moduli from 3D images [Arms, 2002], and computation of conductivity from 3D images [Spanne et al, 1994]. While computational rock physics can provide a useful substitute for laboratory measurements in difficult-to-measure rocks, it does not go beyond providing information about the particular rock sample that was imaged or digitally constructed. Specifically, it does not specify a relationship between geophysical and reservoir properties that can be applied in hydrocarbon exploration to other rocks of the same formation.

From the foregoing, it can be seen that there is a need in hydrocarbon exploration for a method that can determine relationships among seismic, electrical, and reservoir properties in complicated rocks where current methods cannot isolate the effects of each compositional class. Preferably, such a method should be able to quantify the impact of each of a large number of compositional classes on the effective properties of a rock, even with a limited supply of rock samples. The present invention satisfies this need.

SUMMARY OF THE INVENTION

In one embodiment, the invention is a method for developing a model for hydrocarbon exploration of at least one effective material property of a hydrocarbon reservoir as a function of the composition of the reservoir rock, comprising: (a) obtaining one or more rock samples, wherein the sample or samples are characteristic of the compositional classes existing in the reservoir rock, (b) obtaining at least one 3D image of the one or more rock samples, (c) segmenting the 3D image into compositional classes having similar properties, (d) creating for each sample a local properties volume for a selected material property specifying a local value of the selected property at each point throughout the sample, (e) selecting the mathematical form of a model to use for the effective value of the selected material property, where the model has at least one unknown parameter, (f) determining the unknown parameters of the model so that the effective material property values predicted by the model match those computed numerically based on the local properties volumes, and (g) using the model to assess the commercial potential of a subsurface reservoir. In various embodiments, this method can be applied when the selected material properties are, for example, elastic moduli, conductivity, or permeability.

DETAILED DESCRIPTION OF PREFERRED EMBODIMENTS

Figure 1:
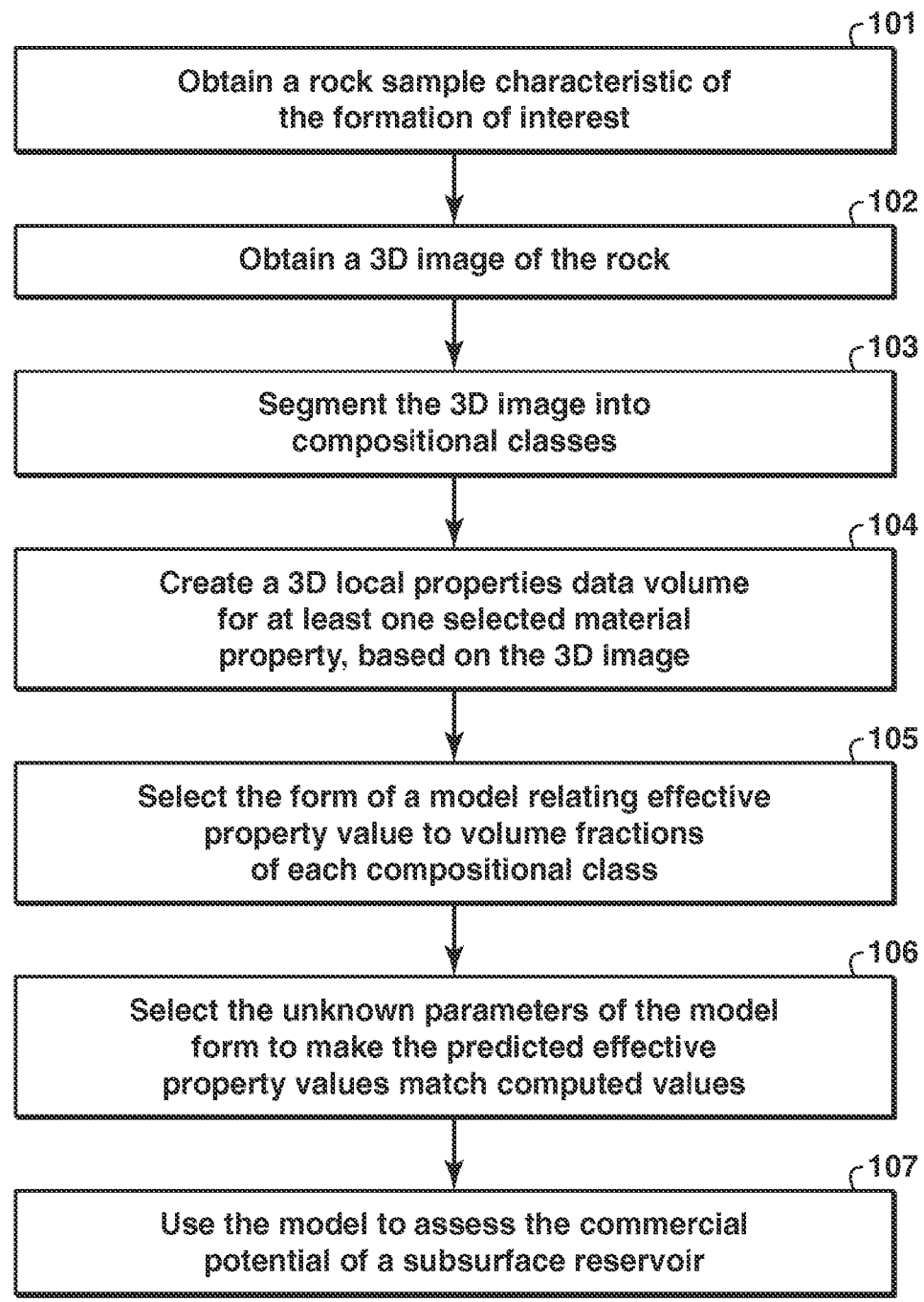
FIG. 1 is a flow chart of an embodiment of the invention.

The present invention is a method for determining relationships for use in hydrocarbon exploration among seismic, electrical, and reservoir properties of a subsurface rock formation. The inventive method allows these relationships to be determined using as few as one rock sample. For a selected property of interest, the inventive method determines a model relating the effective property value to the volume fractions of the compositional classes in the rock. To do this, a 3D image of the rock sample is obtained and segmented into compositional classes. A mapping is determined that converts the 3D image into a local properties volume, specifying the local value of the property of interest at each pixel location. An effective medium model is selected that will ultimately relate the volume fractions of each compositional class to the effective property value for rocks having similar structure to the sample. Such models typically have unknown parameters that must be calibrated using actual rock samples. The inventive method calibrates the model parameters so that the model correctly predicts property values obtained by "virtual measurements" computed from the local properties volume. Once the model parameters are thus calibrated, the model gives a relationship between a selected property of interest and the volume fractions of the compositional classes. Finally, the calibrated model may be applied to assess the commercial potential of a subsurface reservoir, typically by relating a property of the reservoir to seismic or electrical property measurements from surface geophysical surveys or well logs. When more than one property of interest is not a simple function of the volume fractions of the compositional classes, then the inventive method is typically applied to relate each property of interest to the same compositional classes in the rock, and the resulting models solved to determine the relationship between all properties of interest.

In one embodiment, a significant feature of the inventive method is the use of virtual measurements to determine model parameters. Unlike conventional lab measurements, numerical virtual measurements have access to the full 3D structure of the sample and the 3D fields (e.g., stresses and strains, potentials, local flow vectors) within the sample. Thus, virtual measurements can be designed to probe precisely the sensitivity of the effective properties to each compositional class. Examples of virtual measurements include calculating average stresses and strains within a single compositional class or computing effective properties on an altered local properties volume where the properties of a single compositional class are changed.

Numerical finite element software can be used to compute the effective properties of a sample from its local properties specified at each point, as is done in computational rock physics. A premise of the invention is that models that express effective properties as functions of rock composition and structure are approximate expressions for the complicated averaging operation performed by numerical finite element software or other numerical computation that determines effective properties from a local properties volume. Therefore, the numerical simulation can provide a powerful tool for quantifying the parameters of the models when it is applied to a local properties volume that is calibrated to lab measurements, particularly when it is applied to provide virtual measurements that could not be obtained by conventional lab techniques, such as measurements of average fields within a single compositional class or measurements on altered local properties volumes where the alterations correspond to known changes in parameters of the model.

Various types of models could be employed in the inventive method to characterize the relationship between an effective material property of the sample and the volume fractions of the compositional classes. The use of any such model is within the scope of the invention. These models could be based on some simplifying physical approximations, as with theoretical models based on differential effective medium (DEM) theory or self-consistent (SC) theory. Alternatively, the functional forms used in empirical models could be employed. For example, the slope and intercept of a linear curve fit could be determined by the inventive method. In the preferred embodiment, the models give an effective property (e.g., the effective elastic moduli, effective permeability, effective conductivity of the sample) as a function of the volume fractions of each compositional class. The models typically require local values within each compositional class of the same property for which an effective value is desired (e.g., elastic moduli, permeability, conductivity for each compositional class). These local values are typically determined based on the mineralogy of the compositional class and assumptions or measurements related to subresolution structure within the compositional class. The models also typically include geometrical parameters characterizing the structure and spatial distribution of each compositional class (e.g., effective aspect ratios, connectivity, pore sizes, surface areas). In current approaches, these geometrical parameters are assumed based on past experience or determined by calibration to lab measurements. In an embodiment of the inventive method, these geometrical parameters are determined with improved accuracy by computational analysis of the local properties volume.

In a preferred embodiment of the invention, the model assumes a rock sample with N compositional classes, where $v_i$ is the volume fraction and $L_i$ is the material property matrix (e.g., stiffness, conductivity, permeability) for the ith such class. A stimulus applied to the sample generates internal fields within the sample characterized by an intensity (e.g., strains, electric potentials, or pressure gradients) and a flux (e.g., stresses, electrical currents, or flow velocities). The flux field vector averaged over the whole sample, $\sigma$, is related to the intensity field vector averaged over the whole sample, $\in$, by the effective material property matrix $L^*$, as $\sigma = L^* \in$. Furthermore, within the ith compositional class, the averaged flux field vector $\sigma_I$ is related to the averaged intensity field vector $\in_i$ by the material property matrix $L_i$, $$\sigma_i = L_i \in_i. \quad (1)$$

When elements within the ith compositional class have a distribution of properties, $L_i$ is an effective properties matrix and can be determined from the computed intensity and flux fields in the sample according to equation 1. The symmetry of the compositional class determines the number of free parameters in $L_i$, generally much smaller than the number of elements [Torquato, 2002]. However, if equation 1 does not provide enough constraints to determine the free parameters in $L_i$, then different stimuli can be applied to the sample to produce different values of $\sigma_i$ and $\in_i$ and thus additional constraints on $L_i$.

Following Berryman (1997), a matrix $A_i$ can be defined for the $i^{th}$ compositional class such that, $$\in_i = A_i \in. \quad (2)$$

Then the effective material property matrix $L^*$ for the sample can be written as, $$L^* = \sum_{i=1}^{N} v_i L_i A_i. \quad (3)$$

Equation 3 is a model relating the effective material property to the volume fractions of the compositional classes, but the matrix $A_i$ is unknown and varies with the volume fractions of the compositional classes and their material properties. In one embodiment, a theoretical form is assumed for $A_i$, and the free parameters of this form are selected to satisfy equation 2. For many material properties, an approximation to $A_i$ based on spheroidal inclusions is available, where the parameters of the approximation are $L_i$, $L^*$, and the aspect ratio of the spheroids [Torquato, 2002]. Using this approximation for $A_i$, effective aspect ratios for all compositional classes may be determined to satisfy equation 2. Alternatively, the effective aspect ratios can be determined by altering the material properties within one compositional class at a time (altering $L_i$), recomputing the effective property value of the local properties volume for each alteration (computing $L^*$), and selecting the aspect ratios in the approximation to $A_i$ to best satisfy equation 3. Approximations for $A_i$ can be made using additional or different parameters. All such models for $A_i$ are within the scope of this invention.

The present inventive method is an improvement over empirical studies, as it requires only one sample (instead of many) and that sample may have different volume fractions of the compositional classes than the prospective reservoir. Indeed, the present inventive method can be used with a collection of samples in which no one sample contains all the compositional classes in the reservoir, as long as each compositional class is either found in at least one of the samples or is understood well enough that its parameters are known. This flexibility in the number and choice of samples is not available with empirical studies.

The present inventive method is an improvement over techniques commonly used to determine parameters (e.g., aspect ratios) of theoretical models because the computational analysis of the local properties volume directly quantifies the contribution of each compositional class to the effective properties of the sample. For complex rocks, the model parameters that capture those relative contributions cannot be accurately determined from measurements of effective properties alone. Without computational analysis of a 3D local properties volume, there is too much ambiguity between the effects of the compositional classes.

The present inventive method is an improvement over techniques that simulate the processes of rock formation, as it is based on actual observed rock structure and does not depend on the accuracy of process simulations to determine structure. While process simulations are improving in accuracy and show promise for characterizing many siliciclastic rocks, they are relatively untested on predicting the more complicated structures found in carbonates.

Finally, the present inventive method is an improvement over the current applications of computational rock physics, in that it directly determines models for hydrocarbon exploration that specify relationships between geophysical and reservoir properties, rather than simply computing the effective properties of selected samples. Most current applications of computational rock physics over-predict effective elastic properties because they do not adequately characterize sub-resolution structure such as microporosity and grain contacts. In one embodiment, the inventive method solves this problem by forming the local properties volume based on a model that characterizes sub-resolution structure and is calibrated to lab measurements so that effective property predictions are not biased. In current applications of computational rock physics, the value of altering the local properties volume within compositional classes to better constrain model parameters is not recognized, but in one embodiment the present inventive method uses such alterations to constrain all parameters of the model from a single rock sample.

An embodiment of the present inventive method will now be described. With reference to the flow chart of FIG. 1, this embodiment involves procedures to determine the functional relationship between seismic properties and reservoir properties within a rock formation. The seismic properties considered in this embodiment are the effective elastic moduli, and the reservoir properties considered are the porosity and composition of the formation as expressed by the volume fractions of the compositional classes. As illustrated in FIG. 1, a rock sample is obtained that is characteristic of a formation of interest (step 101). A 3D image of the rock sample is obtained (step 102). The image of the rock sample is segmented into the compositional classes that compose the sample (step 103). A 3D local elastic properties data volume is created from the 3D image specifying elastic moduli throughout the rock sample (step 104). The form of a model is selected to relate the effective elastic properties and the volume fractions of each compositional class in the formation of interest, where the model form contains at least one unknown parameter (step 105). Values for the unknown parameters of the model in step 105 are selected to make the effective elastic properties predicted by the model match those computed from the 3D local elastic properties data volume (step 106), and the model is used to assess the commercial potential of a subsurface reservoir (step 107). The individual steps will be described in greater detail in the following paragraphs.

Step 101 is selecting a rock sample that is characteristic of the formation of interest. The rock sample should be selected from the reservoir of interest or from an analog formation having similar composition and structure to the reservoir of interest. The rock sample is typically core plug size (a cylinder 1" diameter×2" long) or smaller, though the dimensions of the sample will be determined by the constraints of the imaging modality and the scale of structure within the sample. The sample should be large enough to contain a statistically representative sampling of the heterogeneity which is to be characterized. For example, a sample of sandstone that is composed of sand grains and pore spaces should be about ten grain diameters long or longer in each dimension so that the analysis is not overly influenced by the variable shape, contacts, and orientation of a particular grain.

Figure 2:
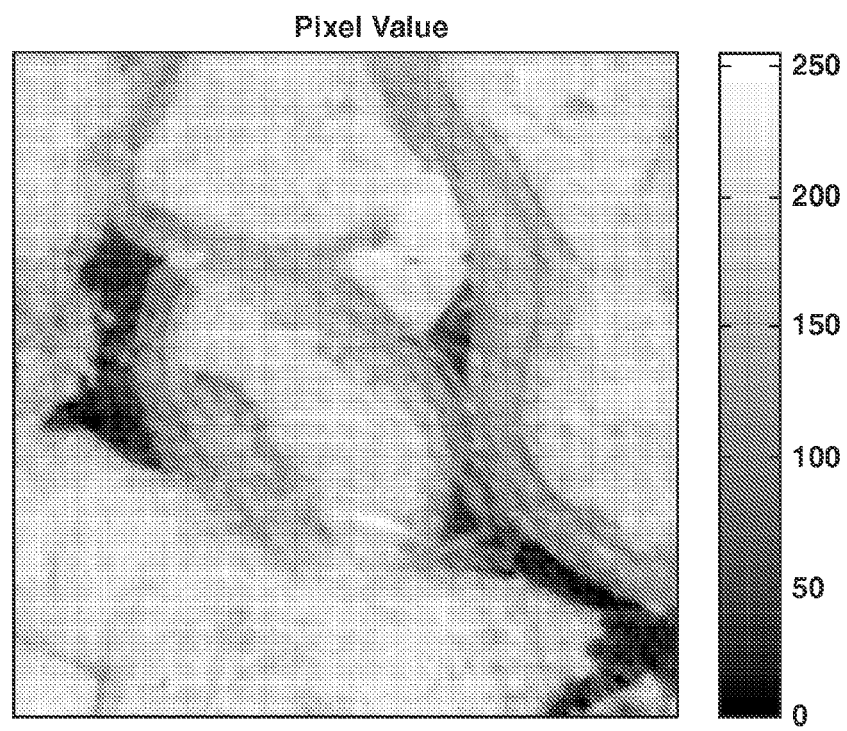
FIG. 2 shows a slice of a 3D X-ray microtomography image of a sample of Indiana Limestone.

Step 102 is obtaining a 3D image of the rock sample. The goal of this step is to obtain detailed information about the structure and composition of the sample. A 3D image necessarily implies that the image represents a quantifiable variation of some material property of the sample throughout its volume. Typically the 3D image is a volume divided into cubic cells called pixels or voxels, where a numerical value corresponding to the imaged material property is assigned to each cell. In a preferred embodiment of the invention, X-ray microtomography is used. [Flannery, et al, 1987] X-ray microtomography provides a 3D image of X-ray linear attenuation coefficient throughout the sample. Each pixel in the image is typically from 1 to 100 microns on a side depending on the system used, and the full image is a 3D data volume of typically 500 pixels on an edge. An example of one slice from such a 3D image is shown in FIG. 2, where the grayscale value of each pixel is related to x-ray linear attenuation coefficient, black being no attenuation and white being maximum attenuation. Other 3D imaging modalities could also be used to image the sample, such as magnetic resonance imaging, focused ion beam imaging, or confocal microscopy. Each of these has its own tradeoffs in resolution, penetration depth, and the material property of the sample represented by the image.

When a true 3D image is not available, there are at least two other ways to create a 3D representation of the sample that can take the place of a 3D image: One such way is to construct a 3D representation of the rock statistically based on a 2D image such as a petrographic thin section. [Nur, 2003] This approach is limited by the assumptions that go into the statistical reconstruction, and certain complicated grain or pore structures may be inadequately represented by the reconstruction. Another way is to construct a 3D representation of a rock by simulation of the processes of deposition, compaction, and diagenesis. [Øren & Bakke, 2002]. In this case, the choice of grain properties, degree of compaction, and nature of diagenesis would typically be guided by a 2D petrographic thin section image of the rock sample. Persons skilled in the field may know of other ways to arrive at a 3D image or 3D representation of a rock sample. All such ways are included within the scope of step 102.

Step 103 is segmenting the image into its compositional classes. Members of a single compositional class should possess the same composition, the same general structure, and the same general location relative to other compositional classes so that they influence to a similar extent the properties of the rock. There is ambiguity in segmenting x-ray attenuation images (to use the X-ray microtomography example) into compositional classes of similar mineralogy because different rock minerals can have similar x-ray attenuations. Segmentation is greatly aided if prior information about the mineral composition of the sample limits the number of possibilities for each pixel. Where there is no prior information, x-ray diffraction can be used to determine mineralogy.

If two compositional classes have equal or nearly equal x-ray attenuations, it may be necessary to use structural metrics to distinguish them. For example, two different types of pores might be distinguished in this way. When a tunable x-ray tomography source is available, x-ray attenuation images at several energies (wavelengths) can be made and the variation in x-ray attenuation with x-ray energy characteristic of the minerals in the sample can be used to more accurately discriminate mineral type. Mineral classification is more difficult with x-ray microtomography systems that utilize a broad spectrum x-ray source. Since x-ray attenuation varies with x-ray energy, the attenuation sensed by broad spectrum sources is the energy-dependent attenuation coefficient averaged over the x-ray energy spectrum as it varies throughout the sample. When mineral discrimination proves too difficult with x-ray tomography alone, x-ray diffraction tomography can be used to directly identify mineral type throughout a sample.

In carbonate rocks, there is often microporosity at a scale below the resolution of x-ray tomography systems. In most rocks there are grain contacts, microfractures, or other subresolution features. X-ray attenuation is related to both the mineral type and porosity within each image pixel. If the mineral type at a pixel is known, then the local porosity at that pixel can be calculated as the percentage by which the imaged x-ray attenuation coefficient is less than the x-ray attenuation coefficient for the solid mineral. Thus, porosity within image pixels with subresolution structure can be accurately determined from x-ray microtomography images, even though the pore structure cannot be seen. When the mineral type at a pixel is uncertain, differences in x-ray attenuation due to mineral type can be confused with differences due to the porosity. Microporosity of accessible pores can be identified by subtracting a tomographic image of a dry rock from an image with an x-ray attenuating dye in the pores. The microporosity of a pixel is calculated as the ratio of attenuation at the pixel in the difference image to the attenuation of the dye.

Step 104 is converting the image or representation of the rock from step 102 into a local elastic properties volume, a 3D data volume which gives the elastic properties (i.e., the bulk modulus and shear modulus) at each point within the sample. The image of the rock provides a 3D representation of the imaged material property—x-ray linear attenuation coefficient in the case of x-ray microtomography. A mapping must be determined that relates the imaged material property to the required elastic properties. A separate mapping will preferably be determined for each compositional class identified in step 103. For classes that are solid mineral, a simple mapping might be to assign the known elastic properties of the mineral to every pixel within the class. Similarly, for classes that are empty pore, a simple mapping would be to assign the known properties of the pore fluid to every pixel within the class. For classes that contain mineral mixes of varying proportions, microporosity, grain contacts, thin fractures, or other subresolution structures, the mapping must take into account the relationship between x-ray attenuation and elastic properties that those factors create.

A preferred embodiment for determining a mapping from the value of the imaged property (e.g., x-ray attenuation) to the local elastic properties, which can be applied to all pixels within a compositional class, is now described. The imaged property value obtained for each pixel is converted to the composition of the pixel (e.g., mineral type and porosity) and then a DEM model specific to the compositional class is used to convert from the composition of the pixel to its elastic properties. The effective aspect ratio for the DEM model is selected to make the numerically computed effective elastic properties for the whole local properties volume match a laboratory measurement of the effective properties of the sample. The required numerical computation is performed using the same numerical software described in step 106. If there is more than one unknown parameter that must be determined, then images and lab measurements on more than one rock sample may be required to determine the unknown parameters. These samples should be selected so that they have different relative abundances of the compositional classes which have models with unknown parameters.

An alternative method for determining a mapping from pixel image value to pixel elastic properties is to apply the inventive method, now at the pixel scale rather than at the sample scale. To apply the inventive method, a higher resolution image of a sample of the compositional class is obtained. The image can come from a piece of the rock sample under study or from an instance of the same compositional class in an analog formation. In the preferred embodiment, a 3D focused ion beam image would be used. Other 3D imaging modalities offering the required resolution can be substituted. Alternatively, a 2D image from a scanning electron microscope or other high resolution 2D imaging modality can be used to calibrate the statistical construction of a 3D image by the method of Nur [2003], alternatively a geological process simulation can be used to construct a digital rock sample representative of the compositional class by the method of Øren & Bakke [2002]. These alternatives to 3D imaging are described in step 102, and their results will typically be more satisfactory for characterizing a single compositional class than for characterizing the rock sample as a whole. Aside from differences in imaging modality, the inventive method can be applied in the same way at the pixel scale as at the sample scale.

At step 105, the mathematical form of the model to be used for relating the elastic properties and reservoir properties is selected. By mathematical form of the model, it is meant the equations or relationships of the model wherein at least one parameter in those equations or relationships is as yet unknown, and will be determined in step 106. A preferred embodiment of the invention uses an SC theory type of model that relates the volume fraction, elastic properties, and an effective aspect ratio for each compositional class to the effective elastic properties of the sample. Embedded in such a model are mineralogy, based on the volume fractions of each compositional class, porosity, which is included among the compositional classes, and some structural information in the form of the effective aspect ratios. The effect of pore fluid changes can be incorporated by Gassmann fluid substitution [Mavko, et al, 2003] after the desired relationships are determined for a single pore fluid type or for the dry rock case. Tight porosity where the "relaxed fluid" assumption behind Gassmann fluid substitution does not hold should be treated as a separate compositional class from the connected porosity, and the elastic properties of the tight porosity should be adjusted to reflect a non-relaxed fluid in the pore space.

Step 106 is to determine the values for the unknown parameters in the mathematical form of the model from step 105, thereby determining the desired relationship among elastic and reservoir properties. The unknown parameters are selected so that the model predicts effective property values that are substantially equal to those computed numerically from the local properties volume. The unknown parameters are adjusted iteratively if necessary until this correspondence is achieved. Skilled persons will recognize that a perfect correspondence between the model prediction and the numerical computation may not be obtainable. In this case, the iterative adjustment of unknown parameter values continues only until the correspondence is as close as is practically possible, i.e. when it is within a selected tolerance or a fixed number of iterations have been tried, or another stopping condition is attained.

Where there is more than one unknown parameter of the model, additional constraints are typically needed to determine the parameters. In a preferred embodiment of the invention, the additional constraints come from the stress field and strain field as computed within the local properties volume, where the six component stress and strain vectors are averaged within compositional classes. The field averages are used to determine the free parameters of a matrix relating averaged strains (or stresses) within a compositional class to averaged strains (or stresses) over the whole sample, as in equation 2. Determining this matrix completes the specification of the unknown parameters in the model of equation 3. In another embodiment, additional constraints are obtained by digitally altering the local properties volume and computing numerically the effective properties of the altered volume. The additional constraints are that the model must accurately predict the computed effective properties for the altered local properties volumes. The local properties volume is altered in different ways and the effective properties of the altered volumes computed numerically until enough constraints are thus produced to accurately determine the unknown parameters of the model. Alternatively, additional rock samples can be used to provide additional constraints. A preferred way to do this is to use all available rock samples including virtual measurements from each of those samples. When the model parameters are overdetermined by virtue of using more than the minimum number of rock samples or more than the minimum number of virtual measurements required to constrain them, estimates of the model parameters from each sample may be averaged (e.g., mean or median). Redundant information about the model parameters may be utilized to improve the accuracy of the final model parameter estimate in various ways familiar to people skilled in statistics.

Alterations applied to the local properties volume are preferably ones that can be accurately and conveniently accounted for by the model. As described in step 105, in the example embodiment of the invention, the model gives effective properties as a function of the volume fractions of each compositional class, an aspect ratio characteristic of the structure and spatial distribution of each compositional class, and the elastic properties (or distribution of elastic properties) of each compositional class. It is difficult to alter the volume fractions of compositional classes in the local properties volume without changing the important structural characteristics of the rock. The aspect ratios are the unknown parameters that are being determined, so these should not be altered. This leaves the elastic properties of the compositional classes. These may be altered with no change to the structure of the rock. In the preferred embodiment, the elastic properties of each compositional class are slightly raised or lowered. Typically, changes of about 20% may be used to provide a perturbation to the effective properties of the sample that is easily distinguishable from computational noise but not large enough to substantially alter the stress and strain distributions within the local properties volume. When altering compositional classes that are pores and have elastic moduli values close to zero, a constant increment is preferably added to the elastic moduli instead of applying a percentage adjustment.

The numerical computation of an effective property value from the local properties volume and the computation of fields within the local property volume is typically accomplished with numerical finite difference or finite element computer programs. Such programs are familiar to persons of ordinary skill in the art. For example, one such program is MELAS3D. [Bohn, 2003] This program computes the effective elastic moduli of the sample from a local elastic properties volume where the local bulk and shear moduli are specified in a grid of cubic cells. The preferred embodiment from the point of view of computational speed would be a computer program that performs the computation on a variable grid optimized to the shape and scale of the elements of the compositional classes and their internal structure, if any. All methods for computing effective properties from the local properties volume are within the scope of the invention.

Finally, the model may be used to assess the commercial potential of a subsurface reservoir (step 107). Practitioners of hydrocarbon exploration rely on models for how geophysical measurements are related to reservoir properties to determine whether a subsurface reservoir contains hydrocarbons, the volume of hydrocarbons in the reservoir, and where to penetrate the reservoir with wells in order to most economically produce the hydrocarbons. These models allow them to determine the critical reservoir properties that cannot be directly measured from surface seismic surveys, electromagnetic surveys, and down-hole measurements in wells. The methods for utilizing such models in hydrocarbon exploration are familiar to persons of ordinary skill in the art.

An example of an embodiment of the invention for modeling elastic properties as a function of macro-porosity and micro-porosity is now described. In this example, a sample of Indiana limestone is selected in step 101 of FIG. 1. Indiana limestone is a monomineralic rock (all calcite) and has both intergranular pores and significant microporosity, especially around the edges of grains. In step 102, the sample is imaged using x-ray microtomography. A 2D slice from the 3D image volume is shown in FIG. 2, where the grayscale value of each pixel is an 8-bit number which is related to x-ray linear attenuation coefficient, black being no attenuation (empty pore) and white being maximum attenuation (solid calcite).

Figure 3:
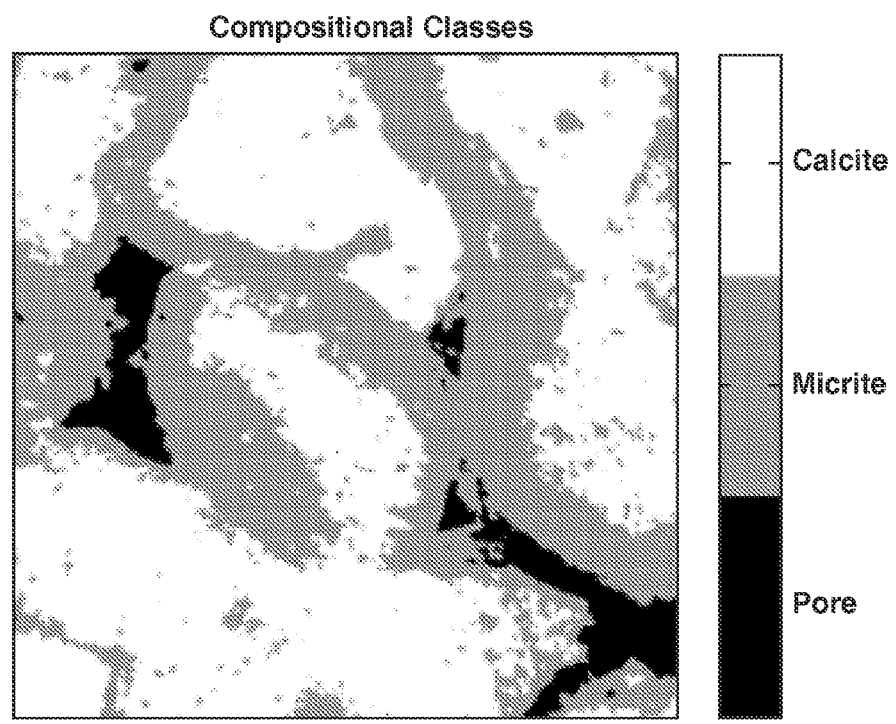
FIG. 3 shows the slice of FIG. 2 now segmented into three compositional classes: solid calcite grains, pores, and microporous calcite (micrite).
Figure 4:
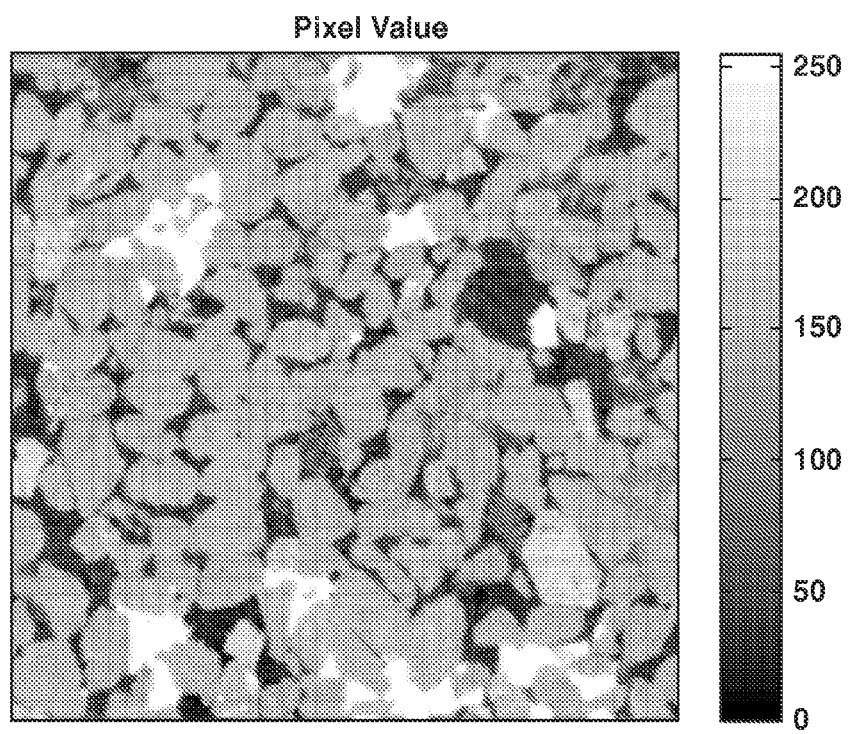
FIG. 4 shows a slice of a 3D X-ray microtomography image of a sample of Berea sandstone.
Figure 5:
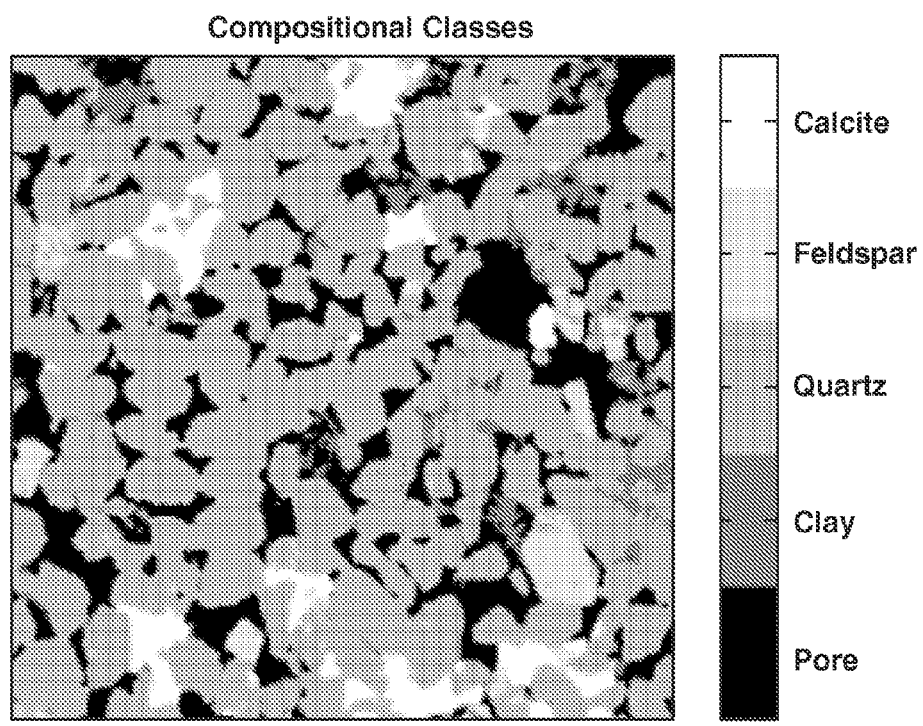
FIG. 5 shows the slice of FIG. 4 now segmented into five compositional classes: quartz grains, feldspar grains, calcite cement, clay, and pores.

Two examples of step 103 are now given. In the first example, the image of Indiana limestone in FIG. 2 is segmented into three compositional classes: solid calcite grains, microporous calcite (called micrite), and open pores. This segmentation is performed simply based on image pixel value. Pixel values from 0 to 70 are considered to be open pores, values from 71 to 180 are considered microporous calcite, and values from 181 to 255 are considered solid calcite grains. The results of the segmentation are shown in FIG. 3. In a second example of segmentation, a 2D slice of a 3D x-ray microtomography image of Berea sandstone (shown in FIG. 4) is segmented into five compositional classes. Berea is known to be composed of quartz grains and feldspar grains, held together with calcite cement, and there is sometimes clay in the pores. The minerals can be distinguished by their x-ray attenuations, so a rough segmentation can be performed based on image pixel value. A rough segmented image is formed by assigning each pixel an integer value from 1 to 5 reflecting its compositional class, then the rough image is filtered by making the center pixel of every 3×3×3 cube of pixels equal to the most common value (mode) within that cube. This mode filter has two desirable effects. First, it reduces speckle due to occasional misclassified pixels. Second, it tends to assign pixels at contacts between compositional classes into one of the two classes, even when they have values between the ranges for those two classes due to resolution limits. FIG. 5 shows the segmentation of FIG. 4.

Figure 6:
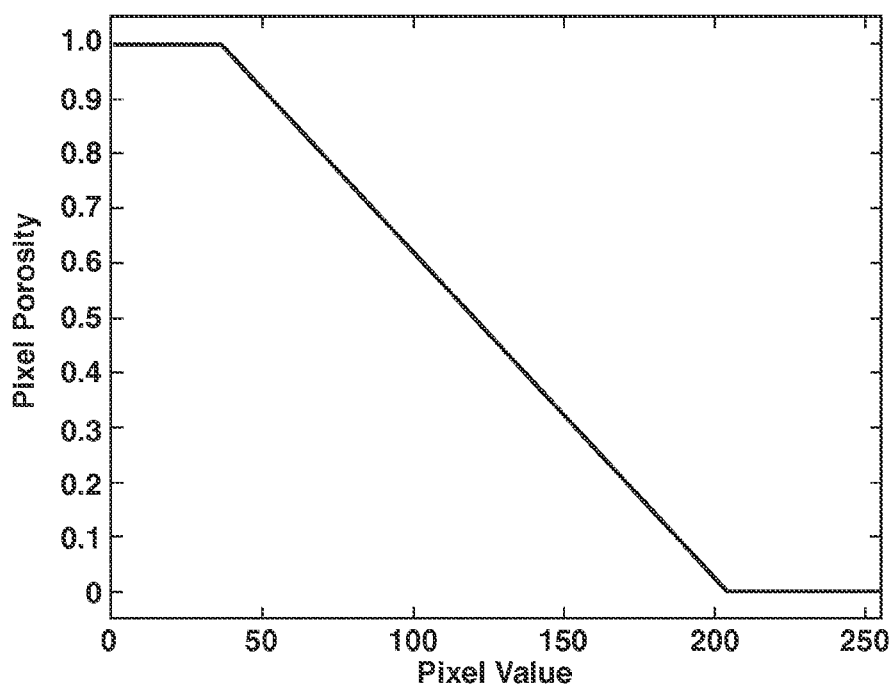
FIG. 6 shows a mapping from image pixel value to pixel porosity.
Figure 7:
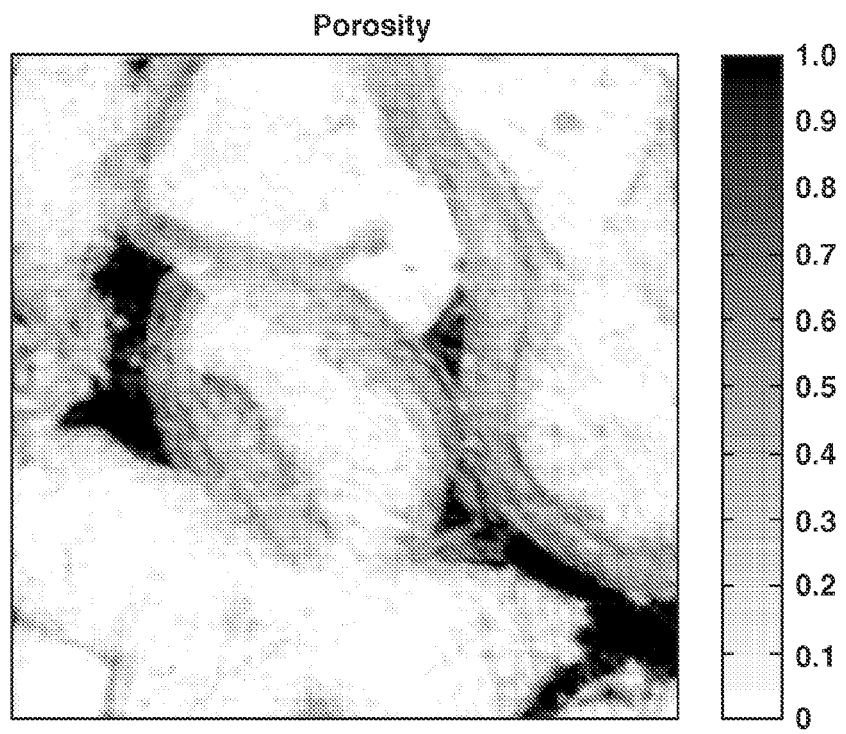
FIG. 7 shows the slice of FIG. 2 where the pixel value has been converted to pixel porosity according to the mapping of FIG. 6.
Figure 8:
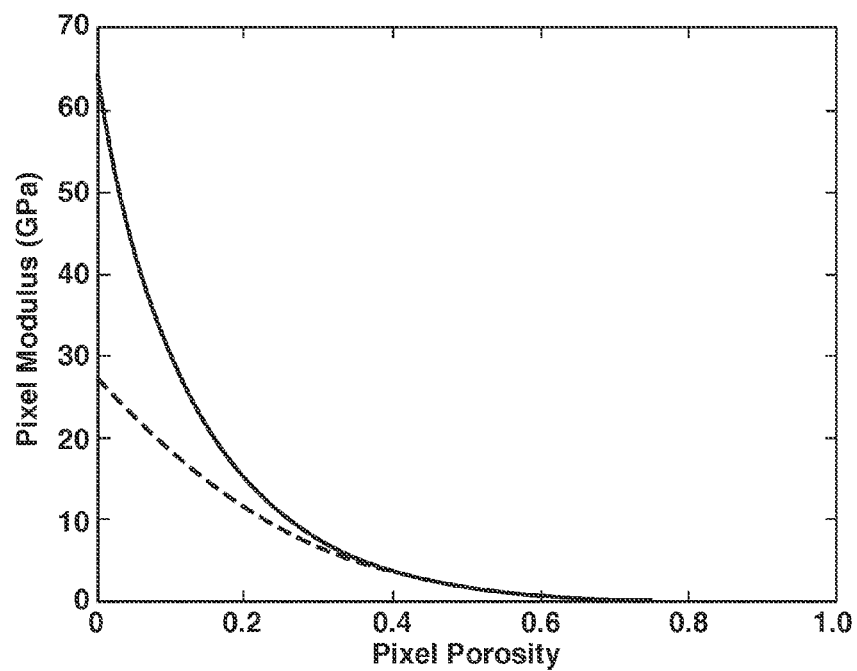
FIG. 8 shows a mapping from pixel porosity to pixel bulk and shear modulus for calcite given a DEM model with an effective aspect ratio of 0.13.
Figure 9:
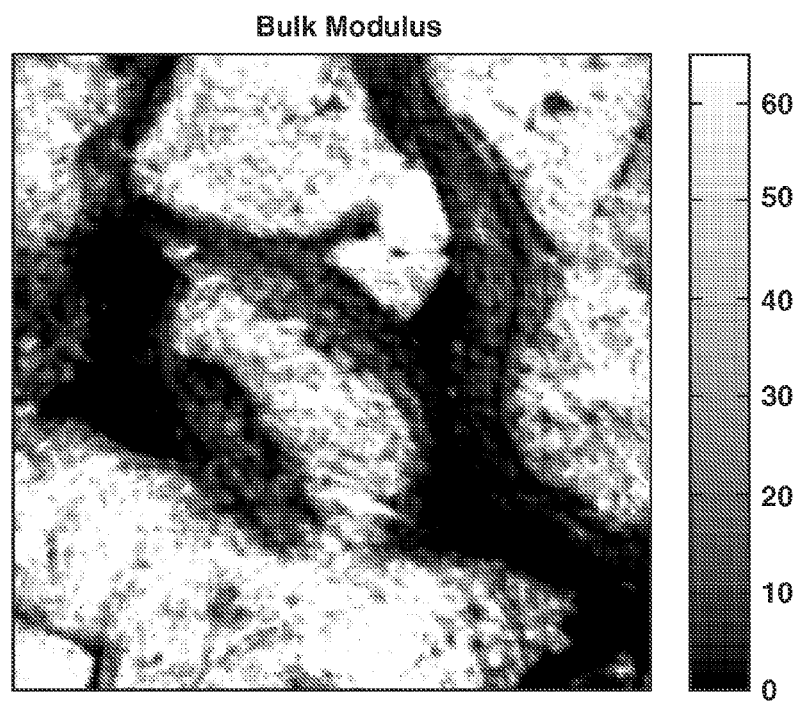
FIG. 9 shows a slice of the local bulk modulus volume which was derived from the porosity slice in FIG. 7 using the mapping of FIG. 8.

An example of step 104 is illustrated by FIGS. 6-9. FIG. 6 shows a relationship between pixel value in a 3D x-ray microtomography image and pixel porosity. FIG. 7 shows the porosity of the image slice in FIG. 2 as calculated from the relationship in FIG. 6. In general, such a relationship would only apply within a single compositional class, but the Indiana limestone used in this example contains only calcite, so pixel porosity and measurement noise are the only variables influencing pixel value. Thus, one relationship between pixel value and porosity can be applied to all compositional classes. Next, pixel porosity from FIG. 7 is converted into pixel elastic moduli according to the relationship in FIG. 8 (the solid line represents bulk modulus and the broken line represents shear modulus) to produce the local bulk modulus volume (FIG. 9) and a local shear modulus volume (not shown). In general, separate relationships would be created for each compositional class and applied only to the pixels in that class. For this monomineralic rock, however, it can be assumed that the relationship is the same in all three compositional classes and apply the one relationship to the whole data volume. The relationship shown in FIG. 8 comes from a DEM model. The required aspect ratio was found by iterative adjustment until the effective elastic properties computed from the local elastic properties volume matched laboratory measurements on the sample. This correspondence was achieved for an effective aspect ratio of 0.13 in this example. This low aspect ratio means the microporous regions are very compliant. Their bulk moduli are much closer to open pore than to solid calcite, as seen in FIG. 9.

In the example, the model selected in step 105 is a DEM model where a single aspect ratio is used for all three compositional classes. The effective properties are computed by starting with a homogeneous medium having the properties of solid calcite, adding 1% of the volume fraction of each pixel value with its associated elastic properties and aspect ratio. This is repeated according to the DEM process until 100% of the volume fraction of each pixel value has been added.

Figure 10:
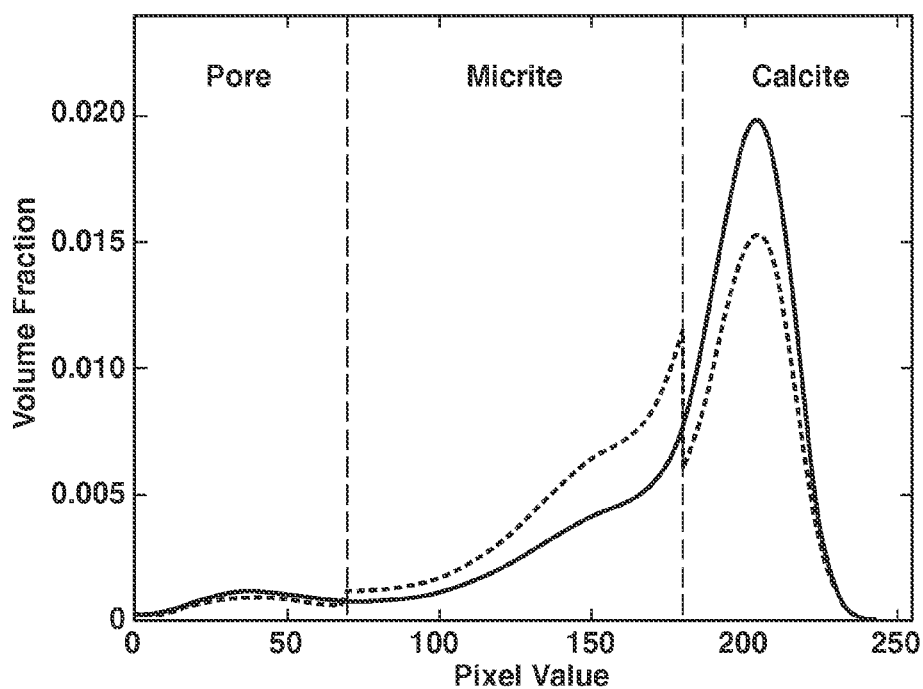
FIG. 10 shows the distribution of pixel values in the sample imaged for FIG. 2 (solid line). The compositional class associated with each range of pixel values is indicated (pore, micrite, calcite). An altered distribution with elevated micrite content is shown by the dotted line.
Figure 11:
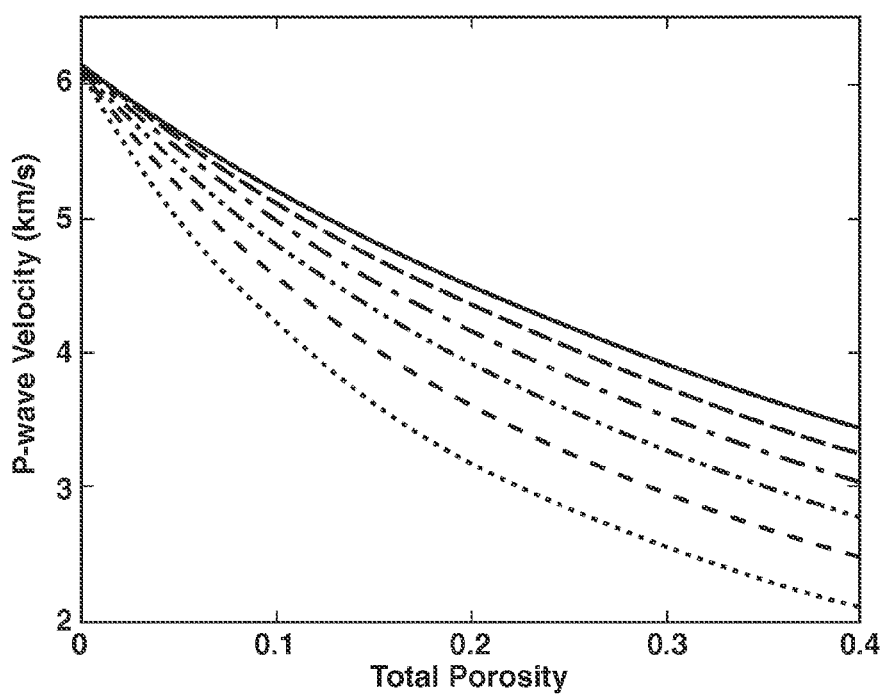
FIG. 11 shows relationships between total porosity (including both the pores and the porosity of the microporous calcite) and compressional wave (P-wave) velocity. The relationship depends on the percentage of the total porosity which is within the microporous calcite.

An example of Step 106 of FIG. 1 is illustrated by FIGS. 10-11. The aspect ratio for the model selected in step 105 is determined to be 0.35. This aspect ratio makes the effective elastic properties predicted by the model match the effective elastic properties computed for the sample based on the local elastic properties volume. In the preferred embodiment, the model would typically have more than one unknown parameter, and additional virtual measurements would be used to constrain the additional parameters. However, this simple one-parameter model is now calibrated and its predictions for the effective elastic properties for rocks with different volume fractions of the compositional classes can be explored. The solid line in FIG. 10 shows the distribution of pixel values in the 3D image from step 102. The segmentation of this distribution into compositional classes from step 103 is superimposed on FIG. 10. The predictions of the model for rocks with different volume fractions of the compositional classes are found by altering the pixel distribution and using the model to calculate the resulting effective properties. An altered pixel distribution is shown by the dotted line in FIG. 10, where the volume fraction of pixels in the micrite class has been increased, and the volume fractions of pixels in the pore class and the calcite class have been decreased proportionally. This process of altering the volume fractions within compositional classes and recalculating the effective properties using the model is repeated to trace out the parametric family of curves shown in FIG. 11 relating seismic wave velocity to porosity. The form of the curve depends on the percentage of total porosity that is micrite. In FIG. 11, the parameter $\%\mu\phi$ (percent of the total porosity which is micrite) increases from the top curve (0%) to the bottom curve (100%) in increments of 20%.

The final step (107) would then be to apply the curves shown in FIG. 12 to make predictions about reservoir properties. Relationships between porosity and velocity might be used, for example, to predict porosity throughout a reservoir based on seismic wave velocities estimated from seismic reflection data.

The present inventive method may also be applied to determine a permeability model instead of an elastic properties model. With reference to FIG. 1, this embodiment of the invention involves procedures to determine the functional relationship between permeability and the volume fractions of the compositional classes within the reservoir rock, i.e. the selected material property in steps 104-106 is permeability instead of bulk/shear modulus. As illustrated in FIG. 1, a rock sample is obtained that is characteristic of a formation of interest (step 101). A 3D image of the rock sample is obtained (step 102). The image of the rock sample is segmented into the compositional classes which compose the sample (step 103). A 3D local permeability data volume is created specifying permeability throughout the rock sample (step 104). The mathematical form of a model with unknown parameters is selected to relate permeability to the volume fractions of each compositional class in the formation of interest (step 105). The unknown parameters of the model form selected in step 105 are determined to match the permeability predicted by the model to the permeability computed numerically based on the 3D local permeability data volume (step 106). Finally, the model with parameters determined in step 106 is applied to assessing the commercial potential of a reservoir. The individual steps will be described in greater detail in the following paragraphs to the extent that the steps differ from the preceding example of the elastic properties model.

Step 101 is performed as in the elastic properties example.

Step 102 is obtaining a 3D image of the rock sample. A preferred embodiment for a permeability model is to use X-ray microtomography to obtain the image [Flannery, et al 1987], but other 3D imaging modalities can be used if they can accommodate the needed resolution and sample size. In the absence of true 3D images, process based approaches for constructing 3D rock models or statistical reconstructions can be tried, though statistical reconstructions may offer less accurate reproductions of permeability than of elastic properties.

Magnetic resonance imaging techniques can image the local permeability volume directly [Bencsik & Ramanathan, 2001], but tend to have lower resolution than x-ray microtomography. When compositional classes with subresolution structure are significant contributors to the effective permeability of the sample, a preferred embodiment is to obtain an x-ray microtomography image for detailed structural information and also utilize the magnetic resonance imaging technique to directly quantify the permeabilities for the compositional classes with subresolution structure.

Step 103 is segmenting the image into its compositional classes. Members of a single compositional class for permeability preferably possess the same composition and the same general structure and spatial distribution so that they influence to a similar extent the effective properties of the rock. The compositional classes preferably are selected so that their volume fractions capture all of the information relevant to determining the effective value of the property of interest. For example, permeability is particularly sensitive to grain size, so when computing permeability, separate compositional classes should typically be used for large and small sized grains and pores. By contrast, elastic properties tend to be less sensitive to grain size, so a size-based division of compositional classes may not be needed when computing elastic properties alone. It is typically possible to perform the segmentation into compositional classes based on image pixel values, though in some cases more advanced imaging (e.g., combining more than one imaging modality) or more advanced image analysis (e.g., geometrical attributes) may be needed.

Step 104 is converting the 3D image or 3D representation of the rock into a 3D permeability model of the rock which gives the permeability at each point within the sample. Solid minerals can be considered to have zero permeability while open pore space poses no obstruction to flow. For compositional classes that have subresolution structure, such as microporosity, grain contacts, or microfractures, the assignment of permeability is more complicated, and a porosity-permeability correlation is used, assigning finite permeabilities to image pixels based on their imaged porosity. If magnetic resonance imaging techniques were applied to image the local permeabilities throughout the sample, then porosity—permeability crossplots can be determined by crossplotting MRI permeability with porosity from X-ray microtomography. If the porosity-permeability relationship is unknown and is a function of one parameter, then a parameter specifying that relationship can be estimated by adjusting it until the computed sample permeability matches laboratory measurements of the sample permeability. If there is more than one compositional class for which a porosity—permeability relationship must be estimated, then at least as many samples are needed as there are compositional classes for which relationships must be determined. Each sample should have the various classes in different relative abundances. Alternatively, the inventive method can be applied at the pixel scale within a single compositional class to determine the required mapping from pixel value to permeability. This alternative requires an imaging modality that can resolve structure at that fine scale.

Step 105 is selection of the mathematical form of the model. The permeability model gives effective permeability as a function of the volume fractions and permeabilities (or permeability distributions) of each compositional class. The permeability model also contains unknown parameters for each compositional class characterizing the structural properties and spatial distributions. A preferred embodiment is a SC model given by Pozniakov [2004], though other alternative models are available and all are within the scope of the invention [Torquato, 2002].

Step 106 is to determine the values for the unknown parameters in the mathematical form of the model, thereby determining the desired relationship between permeability and the volume fractions of each compositional class. The unknown parameters are selected so that the model predicts effective permeability values that are as close as possible to those computed numerically from the local properties volume. The unknown parameters are adjusted iteratively if necessary until this correspondence is achieved. When additional constraints are needed to specify the model parameters, these can be obtained by virtual measurements computed based on the local properties volume.

The numerical computation of permeability may be accomplished by the lattice Boltzmann method. The software implementation of this method preferably allows for cells in the local properties volume that have finite permeability (rather than only passable and impassable cells). Such a capability will be needed for regions of the model with sub-resolution structure and for computing effective permeability of altered local property volumes. An implementation that incorporates this capability is described by Martys [2001]. All methods for computing the effective permeability from the local permeability volume are within the scope of this invention.

Finally, the model may be used to evaluate how to most economically develop a subsurface reservoir (step 107). Practitioners of hydrocarbon exploration rely on models to relate geophysical survey data or well log data to subsurface reservoir properties, including whether a subsurface reservoir contains hydrocarbons, the volume of hydrocarbons in the reservoir, and where to penetrate the reservoir with wells in order to most economically produce the hydrocarbons. When the inventive method is used to determine a permeability model, the inventive method is typically also used to create a seismic/elastic properties model or a conductivity model based on the same compositional classes. The models that relate permeability and another effective property to the same compositional classes can be solved to relate permeability to the other effective property directly, and to determine the extent to which variations in the volume fractions of the compositional classes alter the relationship. For example, the inventive method may applied as in the elastic properties example described above and again as in the permeability example described above. Then the elastic properties model and the permeability model may be solved together to relate elastic properties (expressed as seismic wave velocities) directly to permeability. In this way, a relationship for predicting permeability from geophysical measurements such as seismic data can be constructed, and the error bars on that relationship due to geological variability in the reservoir can be assessed.

The present inventive method may also be applied to determine a conductivity model. With reference to FIG. 1, this embodiment involves procedures to determine for a formation of interest the functional relationship between conductivity and reservoir properties expressed as the volume fractions of the compositional classes. A rock sample is obtained that is characteristic of a formation of interest (step 101). A 3D image of the rock sample is obtained (step 102). The image of the rock sample is segmented into the compositional classes that compose the sample (step 103). A 3D local conductivity data volume is created specifying conductivity throughout the rock sample (step 104). A model with certain unknown parameters is selected for the formation of interest. This model relates conductivity to the volume fractions of the compositional classes (step 105). The unknown parameters of the model selected in step 105 are determined based on numerical analysis of the 3D local conductivity data volume (step 106). Finally, the conductivity model is used to assess the commercial potential of a subsurface reservoir (step 107). The individual steps, to the extent they are different than the other examples, will be described in greater detail in the following paragraphs.

Steps 101, 102, and 103 are performed as in the other examples.

Step 104 is converting the image or representation of the rock into a 3D local conductivity model which gives the conductivity at each point within the sample. Most minerals of the earth's crust have low conductivity. As for pore fluids, oil and natural gas have very low conductivity, while brine or ground water typically has high conductivity. Clays in the presence of brine develop a surface charge distribution which creates a thin high-conductivity layer on the surface of the clay. In rocks with a significant volume fraction of clay, this effect preferably needs to be accounted for in the local properties volume, typically by assigning the water-wet boundary voxels of clay an increased conductivity. For compositional classes that have subresolution structure, such as microporosity, grain contacts, or microfractures, the mapping from the 3D image to the local conductivity volume preferably takes into account the variability in conductivity that those factors create.

A preferred embodiment for relating pixel value to local conductivity within a compositional class is to convert the image pixel value to the porosity of the pixel and then apply a DEM theory model specific to the compositional class to convert from porosity to conductivity. The effective aspect ratio for this model can be selected to make the numerically computed effective conductivity for the whole local properties volume substantially equal to a laboratory measurement of the conductivity of the sample. The required numerical computation of the effective conductivity from the local properties volume is performed using the same numerical software described under step 106 below. If there is more than one unknown parameter in the model for a single compositional class or if there is more than one compositional class in the rock that uses a model with an unknown parameter, then images and lab measurements on more than one rock sample are typically required to determine the unknown parameters. These samples are preferably selected so that they have different relative abundances of the compositional classes that have models with unknown parameters. Alternatively, the inventive method can be applied at the pixel scale within a single compositional class to determine the required mapping from pixel value to conductivity. This alternative requires an imaging modality that can resolve structure at that fine scale.

Step 105 is selection of the type of model to use. In a typical embodiment of the invention, the conductivity model gives effective conductivity as a function of the volume fractions and conductivities of each compositional class. The conductivity model also contains geometrical parameters for each compositional class characterizing the structural properties of the rock. A preferred embodiment uses the SC theory type of conductivity model, though other conductivity models can be substituted [e.g., see Torquato, 2002], and such alternative model choices are within the scope of the invention. The model, like the local properties volume needs to incorporate the effect of boundary charge distributions in rocks with clay content. Appropriate models for this effect are described in Worthington [1985].

Step 106 is performed as in the other examples, except that the numerical computation of effective conductivity is preferably accomplished by the "first-passage-time" method [Torquato, Kim, and Cule, 1999], though conventional finite difference or finite element methods can also be applied. All methods for computing the effective conductivity from the local conductivity volume are within the scope of this invention.

Finally, the conductivity model is used in making decisions about how to manage a reservoir to the greatest economic advantage (step 107). Practitioners of hydrocarbon exploration rely on conductivity models to relate both large-scale surface resistivity survey data and down-hole resistivity measurements to subsurface reservoir properties. Knowledge of reservoir properties is the basis for deciding whether to drill a particular reservoir and where wells should be placed to most economically produce hydrocarbons in a reservoir.

In hydrocarbon exploration, it is often useful to relate effective properties to one another. For example, if permeability can be related to elastic properties and/or conductivity, then geophysical survey data which senses elastic properties and/or conductivity can be used to determine permeability. The inventive method can determine relationships between effective elastic properties, effective permeability, and effective conductivity. To accomplish this, the effective properties of interest are all related to the volume fractions of the same compositional classes within the sample using the embodiments of the invention described above. The models determined in this way then form a system of equations that may be manipulated analytically or solved numerically according to methods familiar to persons of ordinary skill in the art to determine any one of the effective properties as a function of another. The relationship between the effective properties will typically vary depending on the volume fractions of the underlying compositional classes, and this variability can also be determined from the models.

The inventive method can be applied to anisotropic samples where the effective properties and optionally the local properties as well are tensors. If the local properties are tensors, these would be specified in creating the local properties volume in step 104 of FIG. 1. Self-consistent models are available for tensor quantities as described by Willis [1977] and Berryman [1997], and a model of this form would be a preferred embodiment in step 105 of FIG. 1. In step 106 of FIG. 1, the effective properties tensor predicted by the model would be compared with a numerically calculated tensor based on the local properties volume, and additional constraints could be obtained by altering any elements of the local properties tensor within compositional classes and computing the response of the effective properties tensor.

The foregoing application is directed to particular embodiments of the present invention for the purpose of illustrating it. It will be apparent, however, to one skilled in the art, that many modifications and variations to the embodiments described herein are possible. With the benefit of the disclosure herein, persons of ordinary skill in the art will recognize that the inventive method may be applied to relate other effective properties besides seismic properties, permeability, and conductivity to structure and composition. For example, density, magnetic permeability, thermal conductivity, and nuclear magnetic resonance relaxation times can all be related using the inventive method to the structure and composition of rocks. All such modifications and variations are intended to be within the scope of the present invention, as defined in the appended claims. Persons skilled in the art will also readily recognize that in preferred embodiments of the invention, at least some of the steps in the present inventive method are performed on a computer, i.e. the invention is computer implemented. In such cases, the resulting model parameters may either be downloaded or saved to computer memory.

References

Ams, C. H., Knackstedt, M. A., Pinczewski, W. V., and Garboczi, E. J., 2002, Computation of linear elastic properties from microtomographic images: Methodology and agreement between theory and experiment: Geophysics, 67, 1396-1405.

Arns, C. H., M. A. Knackstedt, V. W. Pinczewski, and N. S. Martys, 2004, Virtual permeametry on microtomographic images, J. Petroleum Science and Engineering, 45, 41-46.

Bencsik, M. and C. Ramanathan, 2001, Method for measuring local hydraulic permeability using magnetic resonance imaging, Phys. Rev. E, 63, 065302.

Berryman, J. G., 1997, Explicit schemes for estimating elastic properties of multiphase composites, Stanford Exploration Project Report no. 79. Bohn, R. B. and Garboczi, E. J., 2003, User manual for Finite Element and Finite Difference Programs: A Parallel Version of NIST IR 6269, NIST Interagency Report NISTIR 6997, Building and Fire Research Laboratory, National Institute of Standards and Technology.

Dvorkin, J., and Nur, A., 1996, Elasticity of high-porosity sandstones: Theory for two North Sea data sets, Geophysics, 61, 1363-1370.

Flannery, B. P., H. W. Deckman, W. G. Roberge, K. L. D'Amico, 1987, "Three-dimensional x-ray microtomography" Science 237, 1439-1444.

Greenberg, M. L., and Castagna, J. P., 1992, Shear wave velocity estimation in porous rocks: theoretical formulation, preliminary verification, and applications, Geophys. Prosp., 40, 195-209.

Hoskins, J. C. and J. M. Ronen, 1995, "System and method of predicting reservoir properties" U.S. Pat. No. 5,444,619.

Keehm, Y., Mukerji, T., and Nur, A., 2001, Computational rock physics at the pore scale: Transport properties and diagenesis in realistic pore geometries, The Leading Edge, 20, 180-183.

Knackstedt, M. A., Arns, C. H. and Pinczewski, W. V., 2005, Velocity-porosity relationships: Predictive velocity model for cemented sands composed of multiple mineral phases, Geophysical Prospecting, 53, 1-24.

Kuster, G. T. and Toksoz, M. N., 1974, Velocity and attenuation of seismic waves in two-phase media: Part I. Theoretical formulations: Geophysics, 39, 587-606.

Martys, N. S., 2001, "Improved approximation of the Brinkman equation using a lattice Boltzmann method" Phys. Fluids, 13, 1807-1810.

Nur, A., 2003, "Numerical method of estimating physical properties of three-dimensional porous media" U.S. Pat. No. 6,516,080, Issued Feb. 4, 2003.

Øren, P.-E. and S. Bakke, 2002, "Process based reconstruction of sandstones and prediction of transport properties" Transport in Porous Media 46, 311-343.

Øren, P.-E., S. Bakke, and R. J. Held, 2006, "Pore-scale computation of material and transport properties on North-Sea reservoir rocks", Computational Methods in Water Resources XVI, Copenhagen, Denmark, June 19-22.

Pozdniakov, 2004, "A self-consistent approach for calculating the effective hydraulic conductivity of a binary, heterogeneous medium" Water Resources Research, 40, WO51005.

Spanne, P., J. F. Thovert, C. J. Jacquin, W. B. Lindquist, K. W. Jones, and P. M. Adler, "Synchrotron computed microtomography of porous media: Topology and transports" Physical Review Letters, 73, 2001-2004.

Torquato, S., 2002, Random Heterogeneous Materials New York: Springer.

Torquato, S., I. C. Kim, and D. Cule, 1999, "Effective conductivity, dielectric constant, and diffusion coefficient of digitized composite media via first-passage-time equations" J. Appl. Phys. 85, 1560-1571.

Willis, J. R., 1977, Bounds and self-consistent estimates for the overall properties of anisotropic composite. Journal of Mechanics and Physics of Solids, 25, 185-202

Worthington, P. F. 1985, Evolution of shaley sand concepts in reservoir evaluation. The Log Analyst, 26, 23-40.

The invention claimed is:

1. A method for developing a model for hydrocarbon exploration of at least one effective material property of a subsurface reservoir as a function of the reservoir's rock composition and structure, comprising:
   (a) obtaining a rock sample characteristic of compositional classes existing in the reservoir rock, wherein the rock sample is a core plug or other sample of size equal to or less than a 1 inch diameter by 2 inches long cylinder;
   (b) obtaining a 3D image of the rock sample;
   (c) segmenting the 3D image into at least two compositional classes where regions within each class have similar properties, and wherein the compositional classes are classes of inclusions and voids;
   (d) creating for the rock sample a local properties data volume partitioning the sample into discrete cells, and specifying a value of a selected material property at each cell;
   (e) choosing a mathematical form of a model relating effective, or bulk, value of the selected material property to volume fractions of the compositional classes; and
   (f) determining all unknown parameters of the model by adjusting them, using a computer, to reduce mismatch between effective material property values predicted by the model and effective material property values computed numerically from the local properties volume.

2. The method of claim 1, further comprising using the model to assess the commercial potential of the subsurface reservoir.

3. The method of claim 1, wherein the selected material property is selected from a group consisting of: bulk modulus, shear modulus, compressional wave velocity, shear wave velocity, Vp/Vs ratio, a Lamé constant, and an anisotropy parameter.

4. The method of claim 1, wherein the selected material property is permeability or a component of a permeability vector or tensor.

5. The method of claim 1, wherein the selected material property is selected from a group consisting of: conductivity, resistivity, formation factor, dielectric constant, capacitance, complex impedance, and a component of a complex impedance vector.

6. The method of claim 1, wherein the 3D image is acquired by means of x-ray microtomography, magnetic resonance imaging, focused ion beam imaging, positron emission tomography, or any combination thereof.

7. The method of claim 1, wherein the 3D image is constructed statistically using at least one statistical parameter determined from at least one 2D image of the sample.

8. The method of claim 1, wherein the 3D image is constructed by simulating rock formation processes.

9. The method of claim 1, wherein the 3D image is a pixel display using a parameter characteristic of how the image is acquired or constructed.

10. The method of claim 9, wherein segmenting the 3D image into compositional classes is accomplished using one or more pixel attributes selected from a group consisting of: pixel value, pixel location relative to other pixels with pixel values in a specified range, comparison with pixel values at the same location in a different image, a geometric form exhibited by neighboring pixels with similar pixel values, and any combination thereof.

11. The method of claim 9, wherein the local properties volume is created from the 3D image by applying a mapping relating local properties to image pixel values.

12. The method of claim 11, wherein a separate mapping is used within each compositional class.

13. The method of claim 11, wherein the mapping contains at least one parameter that is determined by matching a computed effective property value from the local properties volume to a measurement of the same effective property value.

14. The method of claim 11, wherein the mapping is based on an effective medium theory.

15. The method of claim 1, wherein the mathematical form of the model is based on an effective medium theory.

16. The method of claim 15, wherein the mathematical form of the model is based on one of: differential effective medium theory or self-consistent theory.

17. The method of claim 1, wherein the numerical computation of effective material property values from the local properties volume is performed on a variable grid adapted to the structure of at least one of: the 3D image, boundaries between compositional classes, and the local properties volume.

18. The method of claim 1, wherein an unknown parameter of the model is determined by comparing a model prediction with a numerical computation on an altered local properties volume.

19. The method of claim 18, wherein the altered local properties volume is formed by altering material property values only within a single compositional class.

20. The method of claim 1, further comprising determining a model relating a second effective material property to the same compositional classes, and using the two models to determine a relationship between the two effective material properties.

21. The method of claim 1 wherein the effective material property is represented by one of: one or more scalar values, a vector, and a tensor.

22. A method for producing hydrocarbons from a reservoir in a subsurface region, comprising:
   (a) obtaining an assessment of commercial potential of the reservoir, said assessment having been performed using steps comprising:
   (i) obtaining a rock sample characteristic of compositional classes existing in the reservoir rock, wherein the rock sample is a core plug or other sample of size equal to or less than a 1 inch diameter by 2 inches long cylinder;
   (ii) obtaining a 3D image of the rock sample;
   (iii) segmenting the 3D image into compositional classes having similar properties, and wherein the compositional classes are classes of inclusions and voids;
   (iv) creating for the rock sample a local properties data volume partitioning the sample into discrete cells, and specifying a value of a selected material property at each cell;
   (v) choosing a mathematical form of a model relating effective, or bulk, value of the selected material property to volume fractions of the compositional classes;
   (vi) determining all unknown parameters of the model by adjusting them to reduce mismatch between effective material property values predicted by the model and effective material property values computed numerically from the local properties volume;
   (vii) using the model to assess the commercial potential of the subsurface reservoir; and
   (b) drilling a well based at least partly on the assessment of commercial potential, and producing hydrocarbons from the well.

23. The method of claim 1, wherein composition of the rock sample is specified in terms of volume fractions of classes comprising one or more of pores, quartz grains, feldspar grains, other grains, calcite cement, other cement, and clay, and sub-classifications of any of these.

* * * * *